US008428219B2

(12) United States Patent
Friedrich (10) Patent No.: US 8,428,219 B2
(45) Date of Patent: Apr. 23, 2013

(54) RADIATION THERAPY DEVICE

(75) Inventor: Werner Friedrich, Ebermannstadt (DE)

(73) Assignee: Siemens Aktiengesellschaft, München (DE)

( * ) Notice: Subject to any disclaimer, the term of this patent is extended or adjusted under 35 U.S.C. 154(b) by 315 days.

(21) Appl. No.: 12/777,770

(22) Filed: May 11, 2010

(65) Prior Publication Data

US 2010/0290586 A1    Nov. 18, 2010

(30) Foreign Application Priority Data

May 18, 2009  (DE) .......................... 10 2009 021 740

(51) Int. Cl.
*A61N 5/10* (2006.01)
*H05G 1/70* (2006.01)

(52) U.S. Cl.
USPC ............................................. 378/65; 378/92

(58) Field of Classification Search .............. 378/4–20, 378/65, 68, 69, 91, 92, 98.8, 114–116, 119, 378/121, 122, 124, 134, 204, 210, 901; 600/425–429; 250/370.01, 370.08, 370.09, 250/371; 977/949–951, 963
See application file for complete search history.

(56) References Cited

U.S. PATENT DOCUMENTS

| | | | |
|---|---|---|---|
| 6,778,850 B1* | 8/2004 | Adler et al. | 600/427 |
| 7,567,647 B1* | 7/2009 | Maltz | 378/21 |
| 2007/0165779 A1* | 7/2007 | Chen et al. | 378/65 |
| 2008/0205588 A1 | 8/2008 | Kim | |
| 2009/0086889 A1* | 4/2009 | Hashemi et al. | 378/22 |
| 2009/0296886 A1* | 12/2009 | Maltz et al. | 378/65 |

OTHER PUBLICATIONS

German Office Action dated Apr. 7, 2010 for corresponding German Patent Application No. DE 10 2009 021 740.1-35 with English translation.
Wang, Q. H. et al., "Field emission from nanotube bundle emitters at low fields," American Institute of Physics, Jun. 16, 1997, pp. 3308-3310.
de Heer, Walt A. et al., "A Carbon Nanotube Field-Emission Electron Source," Science, vol. 270, Nov. 17, 1995, pp. 1179-1180.
Iijima, Sumio, "Helical microtubules of graphitic carbon," Letters to Nature, vol. 354, Nov. 7, 1991, pp. 56-58.

* cited by examiner

*Primary Examiner* — Anastasia Midkiff
(74) *Attorney, Agent, or Firm* — Lempia Summerfield Katz LLC (57) ABSTRACT

A radiation therapy device having a therapeutic radiation source and an imaging unit is provided. The imaging unit includes a plurality of diagnostic radiation sources, from which diagnostic X-ray radiation are directed onto an object to be examined, and a diagnostic radiation detector, with which the diagnostic X-ray radiation is detected after passing through the object to be examined. The plurality of diagnostic radiation sources are X-ray radiation sources that are based on carbon nanotubes. A radiation therapy device having a housing, in which a diagnostic radiation source, a diagnostic radiation detector, and a therapeutic radiation source that is rotated in one plane are arranged, is also provided. The diagnostic radiation source and the diagnostic radiation detector are arranged in the housing such that diagnostic X-ray radiation, which is directed by the diagnostic radiation source onto the diagnostic radiation detector, travels at an angle through the plane.

22 Claims, 5 Drawing Sheets

RADIATION THERAPY DEVICE

This application claims the benefit of DE 10 2009 021 740.1 filed May 18, 2009, which is hereby incorporated by reference.

BACKGROUND

The present embodiments relate to a radiation therapy device having an imaging unit, which is used principally for the treatment of tumor diseases. With the aid of the imaging unit, the anatomy of a patient to be treated may be displayed.

Radiation therapy devices are used for the treatment of tumor diseases, for example. Radiation therapy devices generally generate a beam of therapeutically effective X-rays (e.g., megavolt (MV) X-rays), which is directed at the region to be irradiated in a patient. Instead of X-rays, other therapeutically effective beams may be used (e.g., electron beams or beams of other charged particles).

In order to irradiate the region to be irradiated as precisely as possible and to avoid damaging surrounding tissue, it is important that a patient is positioned as precisely as possible with respect to the treatment beam. For this purpose, a method for performing an imaging process, which enables a patient to be monitored before or during a radiation therapy session, is known.

In this situation, the imaging can be implemented with the aid of X-rays which, originating from a radiation source, are directed onto the patient to be examined and are subsequently detected by a radiation detector. Generally, the X-rays that are used for imaging purposes have a considerably lower energy than those X-rays that are used for the therapy. Such diagnostic X-rays are also referred to as kilovolt (kV) X-rays. A method, however, is also known for using the therapeutically effective MV X-rays for imaging purposes.

Different arrangements are known with regard to how diagnostic radiation sources and diagnostic radiation detectors can be arranged in a radiation therapy device.

A method is thus known, for example, for using an electronic portal imaging device (EPID) in order to register two-dimensional images from a viewing direction that corresponds to the therapy beam path. Two-dimensional X-ray images or fluoroscopy images can likewise be used for position checking.

Using three-dimensional imaging such as, for example, cone beam computer tomography (CT) or conventional CT is also known.

Different methods are also known for monitoring the movement of a patient during a therapy session. This monitoring can be implemented, for example, with the aid of two-dimensional fluoroscopy images by monitoring internal landmarks or implanted markers (e.g., "fiducial markers") with the aid of two-dimensional imaging in real time and/or with the aid of an external movement signal.

SUMMARY AND DESCRIPTION

The present embodiments may obviate one or more of the drawbacks or limitations in the related art. For example, in one embodiment, a radiation therapy device having an imaging unit, which permits a simple construction and simultaneously enables rapid imaging before and/or during an irradiation process, is provided.

The radiation therapy device according to the present embodiments has at least one therapeutic radiation source and an imaging unit, the imaging unit including a plurality of diagnostic radiation sources, from which diagnostic X-ray radiation may be directed onto an object to be examined, and at least one diagnostic radiation detector, with which the diagnostic X-ray radiation may be detected after passing through the object to be examined. The diagnostic radiation sources are, in particular, X-ray sources that are based on carbon nanotubes.

The present embodiments are based on the idea that in the case of known radiation therapy devices, conventional radiation sources such as, for example, rotatably mounted X-ray tubes having a conventional cathode and a conventional anode, are used. Such X-ray tubes do, however, require a comparatively large amount of space. In order to direct X-ray radiation onto an object from a multiplicity of directions, the X-ray tube is either mounted in movable fashion or generates X-rays from a limited number of directions. The use of a plurality of X-ray tubes is cost-intensive.

The use of radiation sources that are based on carbon nanotubes has the advantage that a large number of different positions, from which X-rays may be generated, can be arranged in a comparatively small space. In addition, the radiation sources can be switched on and off simply and flexibly, with the result that projection image data from a plurality of directions can be generated flexibly and quickly.

X-ray sources that are based on carbon nanotubes are known, for example, from the articles, Iijimia, Sumio. "Helical microtubules of graphitic carbon." *Letters to Nature* 354 (1991): 56-58; de Heer, Walt, A. Châtelain, and D. Ugarte. "A Carbon Nanotube Field-Emission Electron Source." *Science* 270 (1995): 1179-80; and Wang, Q. H., et al. "Field emission from nanotube bundle emitters at low fields." *Appl. Phys. Lett.* 70, 24 (1997): 3308-10, the content of which is hereby incorporated by reference. Such X-ray sources include electron sources that emit electrons by way of a carbon nanotube field-emission.

The plurality of diagnostic radiation sources may be arranged locationally fixed with respect to the radiation therapy device. Locationally fixed may be that the radiation sources maintain a spatial location even if parts of the radiation therapy device (e.g., the therapeutic radiation source) are moved. The diagnostic radiation sources may be arranged locationally fixed in the radiation therapy device. Such an arrangement allows a particularly simple construction of the radiation therapy device, and projection image data may be registered from a plurality of directions.

In one embodiment, the therapeutic radiation source may be arranged in the radiation therapy device, such that the therapeutic radiation source may rotate in one plane (e.g., with the use of a gantry). In this case, the plurality of diagnostic radiation sources may be arranged spatially, such that the X-ray radiation emanating from the plurality of diagnostic radiation sources is angled to the plane. Therefore, the principal axis of the X-ray radiation emanating from a diagnostic radiation source does not run parallel to the plane of rotation but at an angle to the plane of rotation. The plurality of diagnostic radiation sources and the radiation detector may be arranged, such that the X-ray radiation passes through the plane of rotation.

Such an arrangement has the advantage that the construction of the radiation therapy device is simplified because the plurality of diagnostic radiation sources and the radiation detector are arranged outside the plane of rotation.

In one embodiment, the radiation therapy device has a control unit that is designed to control the plurality of diagnostic radiation sources and to read out the at least one radiation detector in coordination with the control of the plurality of diagnostic radiation sources. By using the control unit, a plurality of projection image data for the object may be generated from different directions. This is advantageous if a plurality of diagnostic radiation sources are projecting onto one radiation detector. Through the coordination of the control of the plurality of diagnostic radiation sources and the reading out of the radiation detector, the direction, from which projection image data for the object has been registered in each case, is also known. Three-dimensional information about the object may be ascertained from the registered projection image data and from the associated direction.

For example, three-dimensional image information such as, for example, a cone beam computer tomography may be ascertained from the plurality of projection image data. In order to register projection image data for a cone beam computer tomography, projection image data is registered, for example, over an angular range of more than 180°.

A faster method of obtaining three-dimensional image information is, for example, digital tomosynthesis. In this situation, projection image data from a considerably smaller angular range is registered (e.g., an angular range of 40°). Although projection image data from this angular range does not allow a complete three-dimensional image to be reconstructed, a digital tomosynthesis image may, however, be successfully reconstructed from the projection image data. The digital tomosynthesis image is a two-dimensional image. However, since the location of the section through the object, which the tomosynthesis image maps, is known, the tomosynthesis image also contains "three-dimensional" image information, from which information about the three-dimensional location of the object may be obtained. Using a plurality of tomosynthesis images of differing layer thickness, the third dimension may be mapped, depending on the number of tomosynthesis images with partial depth resolution.

If information about a movement of the object to be mapped is also registered during registration of the projection image data, four-dimensional image information may be reconstructed as described above (e.g., a four-dimensional cone beam CT).

In particular, the control unit of the radiation therapy device may be designed, such that the plurality of diagnostic radiation sources can be controlled while the therapeutic radiation source is activated. In this case, the projection image data may be used in order to ascertain or to monitor the location of the object to be irradiated during an irradiation process. If it is determined, for example, that the location of the object to be irradiated has changed, the irradiation process may be modified accordingly and/or temporarily interrupted.

In one embodiment, the plurality of diagnostic radiation sources are arranged in circular fashion in the radiation therapy device, such that the object to be examined is positioned inside the circular arrangement of the plurality of diagnostic radiation sources. Such an arrangement makes it possible to register projection image data over a wide angular range for the object to be examined.

In one embodiment, the radiation therapy device may be designed such that the radiation therapy device has a housing with a central, approximately circular opening. The form of the radiation therapy device is thus similar to the form of known computer tomographs. The object to be examined, or to be irradiated, is arranged in the central opening. The therapeutic radiation source, the plurality of diagnostic radiation sources and the at least one diagnostic radiation detector are arranged inside the housing.

Such an arrangement has the advantage that the therapeutic radiation source and the diagnostic imaging unit are arranged behind the housing (i.e., not visible to the patient). Especially when parts of the radiation therapy device, such as the therapeutic radiation source, for example, are arranged in movable fashion, this prevents the possibility of a collision taking place with the patient. Such an arrangement is also simple to implement. If, for example, the plurality of diagnostic radiation sources are arranged locationally fixed, and the therapeutic radiation source is rotatably mounted, such an arrangement may be simply implemented in the housing because a single rotatable gantry is arranged in the housing.

In one embodiment, at least one part of the plurality of diagnostic radiation sources shares a diagnostic radiation detector. This embodiment is made possible through the use of X-ray sources that are based on carbon nanotubes because the radiation sources can then be positioned spatially in close proximity, such that a plurality of radiation sources, which are arranged in one angular range, can project onto the same radiation detector.

In one embodiment, a plurality of diagnostic radiation detectors may be arranged in circular fashion around the object to be examined. In this case, one part of the diagnostic radiation sources may be associated with each of the plurality of diagnostic radiation detectors. Accordingly, the number of diagnostic radiation detectors to be used is reduced.

In one embodiment, a radiation therapy device having a housing, in which an imaging unit and a therapeutic radiation source that can be rotated in one plane are arranged, is provided. The imaging unit includes at least one diagnostic radiation source and at least one diagnostic radiation detector, which are arranged, such that diagnostic X-ray radiation directed by the diagnostic radiation source onto the diagnostic radiation detector travels at an angle through the plane.

The diagnostic X-ray radiation or the principal axis of the diagnostic X-ray radiation does not run parallel to the plane of rotation of the therapeutic radiation source but passes at a generally oblique angle through the plane of rotation.

When using such an arrangement, the diagnostic radiation source may be arranged in a fixed location. This has the advantage that the diagnostic radiation source does not require a gantry, with which the diagnostic radiation source is rotated. This considerably simplifies the structural design of the radiation therapy device. Also, the therapeutic radiation source is able to rotate freely.

In one embodiment, an X-ray source that is based on carbon nanotubes may be used as the diagnostic radiation source. Carbon nanotubes may be arranged in space-saving fashion, such that a plurality of carbon nanotubes may be arranged in a fixed location in the radiation therapy device. X-ray radiation that emanates from the diagnostic radiation sources may be directed from a plurality of different directions onto the object, and a plurality of different projection image data may be obtained even though the diagnostic radiation sources are arranged locationally fixed.

Arrangements such as have been described for an embodiment of the radiation therapy device also apply analogously to other embodiments of the radiation therapy device described above. These include, for example, the previously described reconstruction of three- or four-dimensional image information.

DETAILED DESCRIPTION OF THE DRAWINGS

Figure 1:
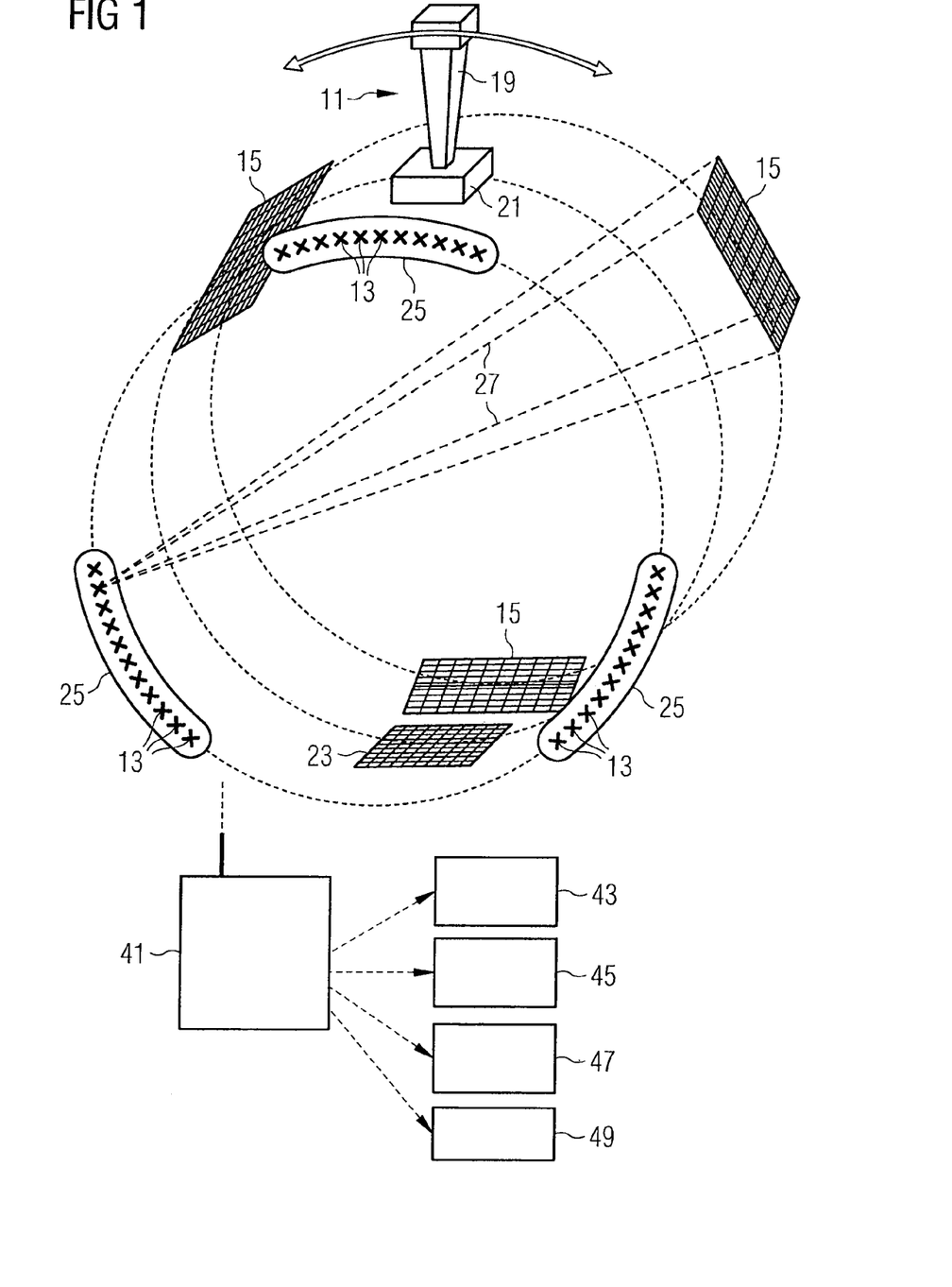
FIG. 1 shows a perspective view of one embodiment of an arrangement of a therapeutic radiation source and an imaging unit.

FIG. 1 shows a perspective view of one embodiment of an arrangement of a therapeutic radiation source 11 and an imaging unit, the imaging unit including a plurality of diagnostic radiation sources 13 and diagnostic radiation detectors 15, in a radiation therapy device.

The therapeutic radiation source 11 generates the radiation with which the irradiation process of an object 17 (which, for the sake of clarity, is represented only in FIG. 2), a phantom or a patient, for example, is performed. The therapeutic radiation source 11 may, for example, include a linear accelerator 19, which is used to accelerate electrons before the electrons strike a target in order to generate the therapeutic X-ray radiation. The therapeutic radiation source 11 may also include a collimator 21, which is used to adjust the cross-section of the therapeutic X-ray radiation to a volume to be irradiated.

In this situation, the therapeutic radiation source 11 is arranged on a rotatable gantry (not shown), such that the therapeutic radiation source 11 may be rotated about an axis. Using the rotatable gantry, the irradiation process may be performed from different angles (e.g., over an angular range of 180° to 360°). The rotation of the therapeutic radiation source 11 defines a plane of rotation. An EPID detector 23 is arranged opposite the therapeutic radiation source 11 on the rotating gantry, such that portal images may be registered.

The plurality of diagnostic radiation sources 13 are arranged on one side of the plane of rotation, displaced parallel to the plane of rotation. The plurality of diagnostic radiation sources 13 are arranged in circular fashion around the axis of rotation of the therapeutic radiation source 11. In the embodiment illustrated in FIG. 1, the plurality of diagnostic radiation sources 13 are grouped into three one-dimensional arrays, arranged in a tube 25 in each case.

The plurality of diagnostic radiation detectors 15 are arranged on another side of the plane of rotation, likewise displaced parallel to the plane of rotation. Each tube 25 is assigned and situated opposite a diagnostic radiation detector 15. In the embodiment illustrated in FIG. 1, the diagnostic radiation detectors 15 are designed as flat panel detectors (e.g., as flat panel detectors made of amorphous silicon). Using one of the radiation detectors 15, X-rays, which emanate from one of the plurality of diagnostic radiation sources 13 of the oppositely situated tube 25 and are directed onto the one radiation detector, may be registered. By way of example, one beam path 27 of the X-rays, which emanate from one of the plurality of diagnostic radiation sources 13 and strike an oppositely situated radiation detector 15, is drawn in.

Figure 2:
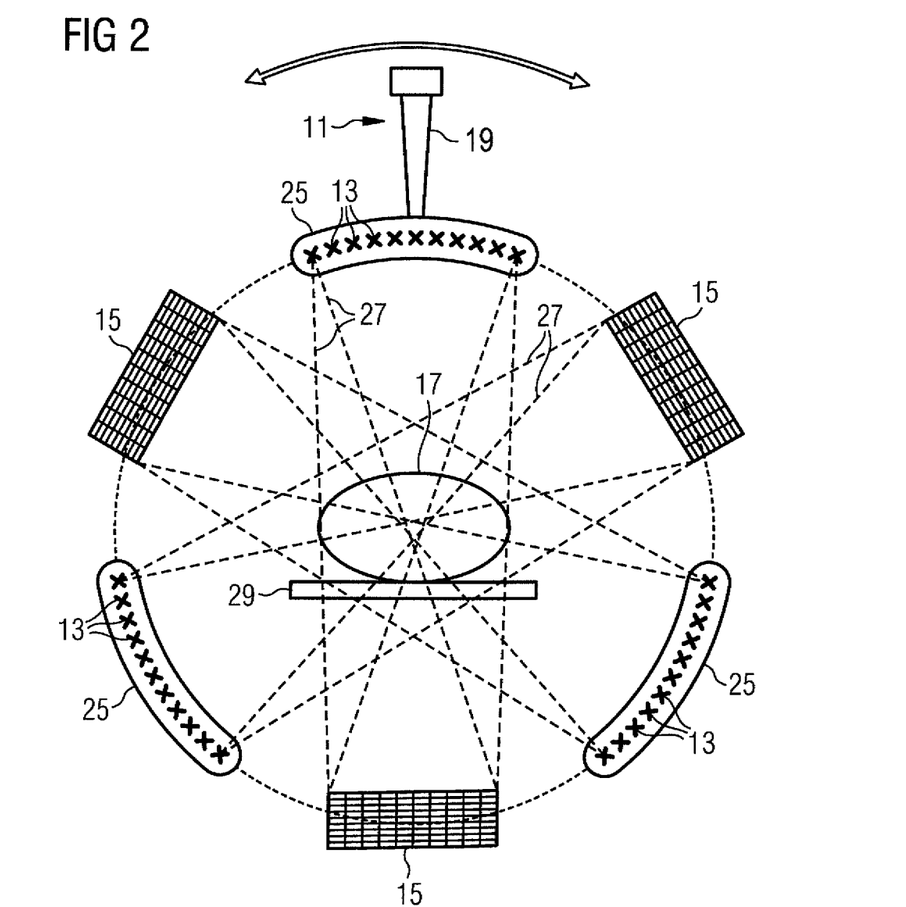
FIG. 2 shows a front view of the arrangement from FIG. 1.

FIG. 2 shows a front view of the embodiment of the arrangement shown in FIG. 1. The circular arrangement of the imaging unit (i.e., of the tubes 25 containing the plurality of diagnostic radiation sources 13 and of the radiation detectors 15) may be clearly seen in FIG. 2. Also shown in this view is the object 17 to be irradiated, which is positioned in the center of the imaging unit on a couch 29, as well as several dashed-line beam paths 27 which emanate from the tubes 25 and strike the oppositely situated radiation detectors 15.

Figure 3:
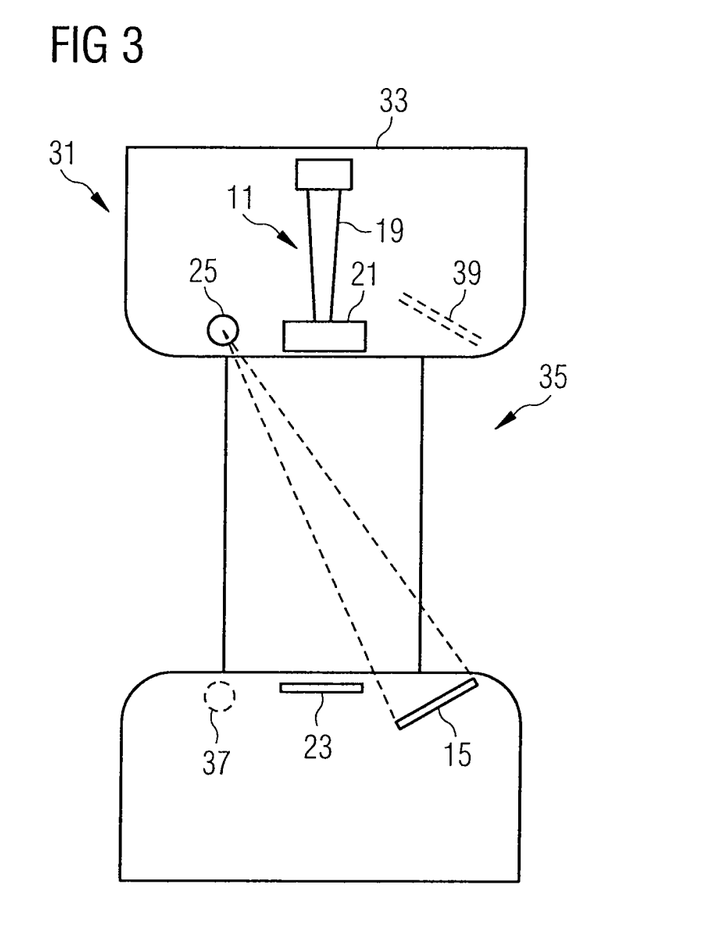
FIG. 3 shows a longitudinal section through a radiation therapy device having an arrangement in accordance with FIG. 1 and FIG. 2.

FIG. 3 shows a longitudinal section of a radiation therapy device 31 having an arrangement in accordance with FIG. 1 and FIG. 2. A housing 33 of the radiation therapy device 31 is also included in this view. An object may be positioned in a cylindrical central opening 35.

Figure 5:
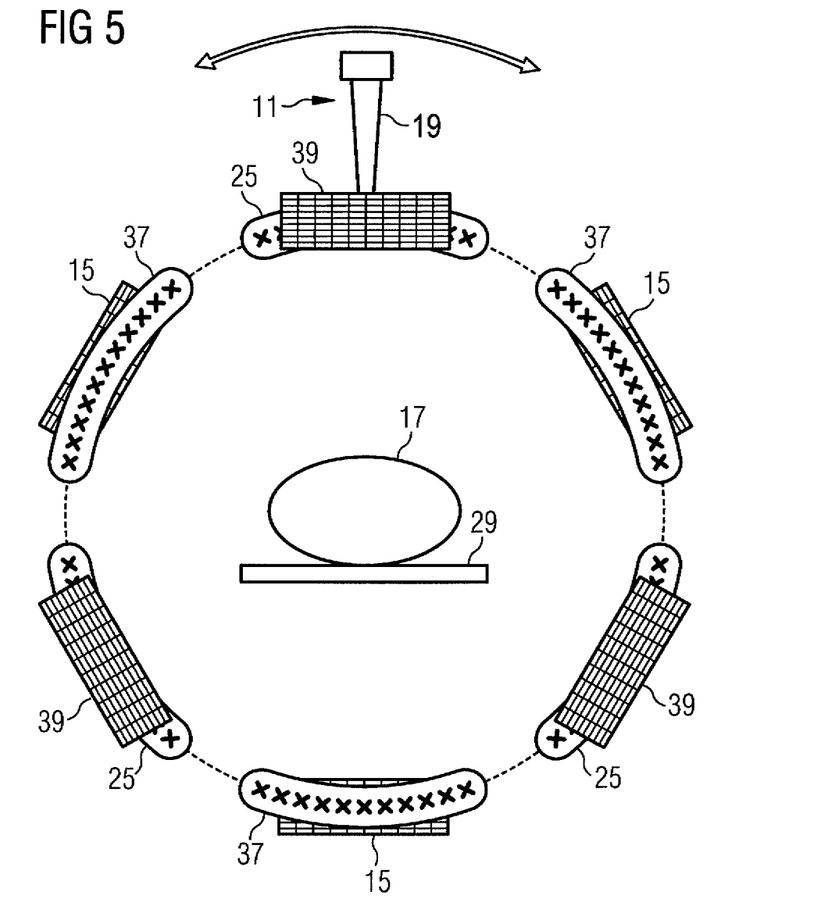
FIG. 5 shows a front view of one embodiment of the imaging unit.

Included in dash-dotted form in this view are a further tube 37 and a further detector 39, which correspond to a longitudinal section through the arrangement illustrated in FIG. 5.

Projection image data for the object 17, which is positioned for the irradiation process in the center of the circular arrangements, may be registered from a plurality of directions by using the arrangement illustrated. For the imaging process and the irradiation process using the therapeutic X-ray source 11, the object 17 does not need to be moved (e.g., the object 17 may remain in the same position).

The radiation therapy device 31 has a control unit 41. In one embodiment, the plurality of diagnostic radiation sources 13 may be individually controlled and activated in order to register the projection image data by using the control unit 41. To this end, the plurality of diagnostic radiation sources 13 are connected with an electronic circuit arrangement (not shown), which provides a high-speed control facility for the plurality of diagnostic radiation sources 13.

The control unit 41 also accordingly controls the readout from the radiation detectors 15 in a coordinated fashion. Using the control unit 41, the direction from which the projection image data has been registered may be associated with the projection image data. This is important for a subsequent image reconstruction.

For the sake of clarity, the control unit 41 is included schematically only in FIG. 1.

In one embodiment, by using the locationally fixed plurality of diagnostic radiation sources 13 designed on the basis of carbon nanotubes, a plurality of projection image data for the object 17 to be examined may be registered within a short period of time. This is in contrast to conventional imaging devices, which require a movement of the diagnostic radiation source.

In one embodiment, the control unit 41 is also designed to process the registered projection image data in order to obtain three-dimensional information with respect to the location of the object to be examined. For example, the control unit may reconstruct a cone beam CT data set 43 or a digital tomosynthesis image 45.

Since the plurality of diagnostic radiation sources 13 may be controlled quickly and individually, the imaging unit is also particularly suited for reconstructing a data set that maps the chronological change in the volume to be examined, such as, for example, a four-dimensional cone beam CT data set 47 or a four-dimensional CT data set. This is possible even if the object to be examined should be mapped in real time during a treatment with the therapeutic radiation source. The speed with which a four-dimensional imaging process can be performed in real time makes it possible to track a target volume online (i.e., in real time) only with the aid of the registered projection image data, even if no markers are implanted in an organ to be irradiated or if no external positioning systems are used for tracking the target volume.

The control unit 41 described here may, as indicated in FIG. 1, be implemented in a single computer unit. Other configurations are possible; thus, the control unit 41 may be distributed among different subunits that assume different functions. For example, one subunit may handle the control of the plurality of diagnostic radiation sources 13, and another subunit may handle the evaluation of the image data and the reconstruction.

The position of the patient to be irradiated or of the tumor to be irradiated may be obtained immediately prior to commencing the treatment with the imaging unit described above.

It is therefore possible to perform a check on the form of the target volume in high quality, quickly and in an uncomplicated manner.

For example, the current location of a tumor may be checked during the irradiation process of a lung, or the location of the prostate, which can shift as a result of intestinal gas accumulations, may be checked. The ability to precisely check the location and form of the target volume and/or the location and form of the patient is particularly advantageous within the scope of stereotactic radiation surgery (SRS), stereotactic radiation therapy (SRT) or stereotactic body radiation therapy (SBRT).

A rapid checking of the location or of the form of the target volume, which may result for example from a shift in the intestinal gas accumulations or from an inadvertent movement of the patient, is also possible during an irradiation process. A rapid checking of the location or of the form of the target volume is also possible while the therapeutic radiation source 11 is active.

In one embodiment, conventional two-dimensional fluoroscopy or X-ray imaging 49 may be performed by activating only individual ones of the plurality of diagnostic radiation sources 13 and correspondingly reading out the oppositely situated flat panel radiation detector or detectors 15. The plurality of diagnostic radiation sources 13, which are used for the fluoroscopy, may be designed to be correspondingly amplified.

As a result of the plurality of differently positioned diagnostic radiation sources 13, a two-dimensional plane for the fluoroscopy or X-ray imaging may be selected with a very high degree of freedom. A direction that is essentially orthogonal to the direction of movement of the object/tumor may be chosen in each case, so that the movement can be monitored particularly precisely. On account of the precise monitoring of movement, a method that is used in order to compensate for the movement may be precisely executed (e.g., gating or tracking).

In one embodiment, as a result of the fact that the plurality of diagnostic radiation sources 13 and the flat panel detectors 15 are in a spatially fixed geometric relationship with one another, a static system for collimating the diagnostic X-ray beam may be used. The locationally fixed arrangement of the plurality of diagnostic radiation sources 13 and the radiation detectors 15 in the radiation therapy device 31 (e.g., in the housing 33 of the radiation therapy device 31) allows the rotating gantry to be more simply designed. Accordingly, the dimensions and the weight of the rotating gantry may be reduced. In addition, the locationally fixed arrangement of the plurality of diagnostic radiation sources 13 and flat panel detectors 15 enables simple cabling and control thereof.

The arrangement illustrated in FIGS. 1 to 3 is merely one example. Many other variants are possible as long as the X-ray radiation emanating from one of the plurality of diagnostic radiation sources 13 is registered by a radiation detector 15.

For example, the number of diagnostic radiation sources 13, which are arranged in one tube 25, or the number of tubes 25 in total may vary. In one embodiment, the plurality of diagnostic radiation sources 13 may be arranged in a single array that extends around 360° in a circular ring form. The flat panel detectors 15 also extend around 360° in a circular ring form. This case is illustrated in a front view in FIG. 4.

Figure 4:
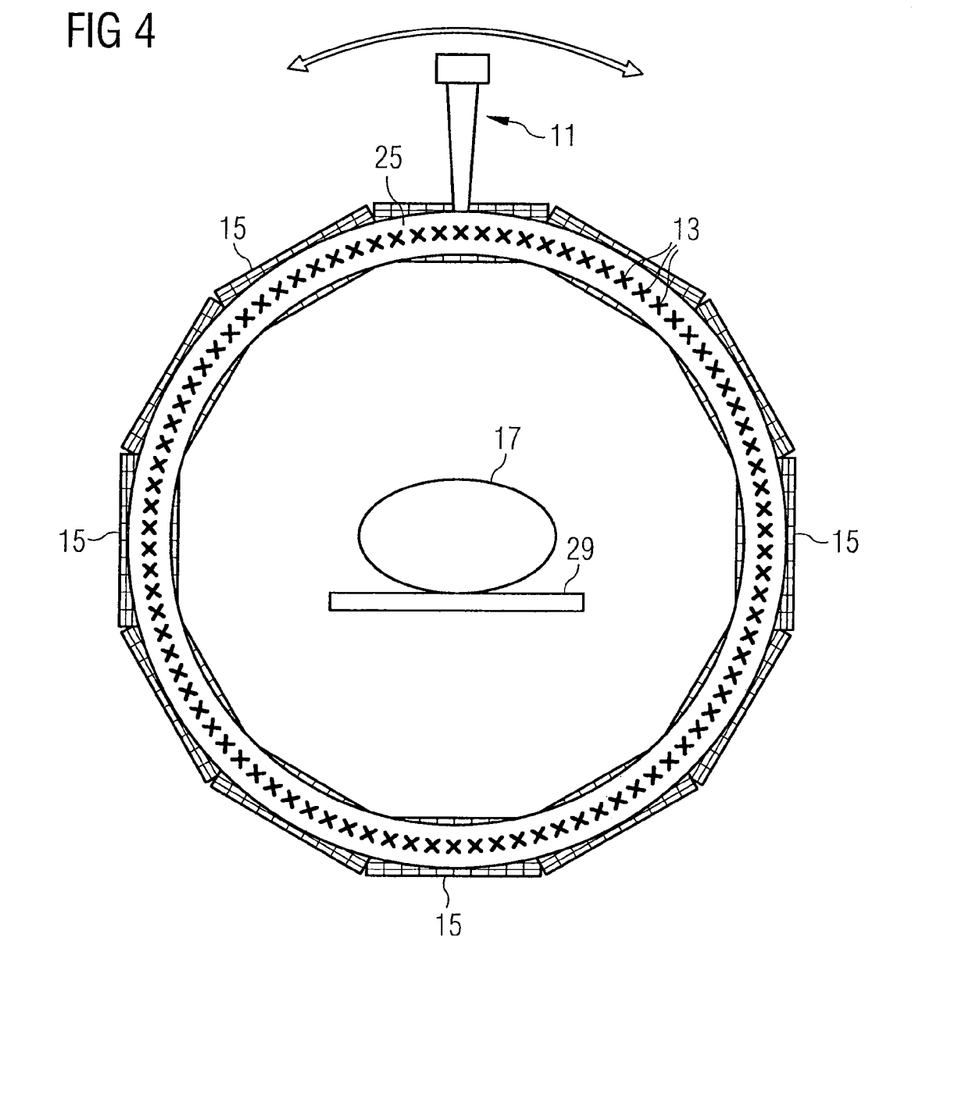
FIG. 4 shows a front view of one embodiment of the imaging unit.

In one embodiment, instead of separate flat panel detectors 15, individual detector elements for X-ray radiation may also be arranged in a circular ring form. For example, the individual detector elements may extend continuously around 360° in a circular ring form.

In one embodiment, the plurality of diagnostic radiation sources 13 as well as the diagnostic radiation detectors 15 may be arranged on one side of the plane of rotation. This case is illustrated in FIG. 5. Further flat panel detectors 39 may be arranged between each of the three tubes 25 illustrated in FIG. 5. The further tubes 37, which are associated with the further flat panel detectors 39, are arranged correspondingly on the opposite side of the plane of rotation, between the radiation detectors 15.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A radiation therapy device comprising:
   a therapeutic radiation source; and
   an imaging unit, the imaging unit comprising:
      a plurality of diagnostic radiation sources, from which diagnostic X-ray radiation is directed onto an object to be examined, wherein the plurality of diagnostic radiation sources are X-ray sources, which are based on carbon nanotubes; and
      a diagnostic radiation detector, with which the diagnostic X-ray radiation is detected after passing through the object to be examined,
   wherein the plurality of diagnostic radiation sources are arranged locationally fixed in the radiation therapy device such that the plurality of diagnostic radiation sources do not rotate when the therapeutic radiation source rotates.

2. The radiation therapy device as claimed in claim 1, wherein the therapeutic radiation source is arranged in the radiation therapy device such that the therapeutic radiation source is operable to rotate in a plane, and
   wherein the plurality of diagnostic radiation sources are arranged such that the X-ray radiation emanating from the plurality of diagnostic radiation sources is angled to the plane.

3. The radiation therapy device as claimed in claim 1, further comprising a control unit configured to control the plurality of diagnostic radiation sources and to read out the diagnostic radiation detector in coordination with the control of the plurality of diagnostic radiation sources, such that a plurality of projection image data for the object are generated from different directions.

4. The radiation therapy device as claimed in claim 3, wherein the control unit is configured to generate three-dimensional image information or four-dimensional image information from the plurality of projection image data for the object to be examined.

5. The radiation therapy device as claimed in claim 3, wherein the control unit is configured to control the plurality of diagnostic radiation sources while the therapeutic radiation source is activated.

6. The radiation therapy device as claimed in claim 3, wherein the control unit is configured to operate the plurality of diagnostic radiation sources in a fluoroscopy imaging mode and to coordinate an activation of one of the diagnostic radiation sources with a direction of movement of the object to be examined.

7. The radiation therapy device as claimed in claim 1, further comprising a circular gantry having a central opening, in which the object to be examined is arranged, wherein the therapeutic radiation source, the plurality of diagnostic radiation sources and the diagnostic radiation detector are arranged inside a housing of the circular gantry.

8. The radiation therapy device as claimed in claim 1, wherein the plurality of diagnostic radiation sources are arranged in circular fashion in the radiation therapy device, and wherein the object to be examined is positioned inside the circular arrangement of the plurality of diagnostic radiation sources.

9. The radiation therapy device as claimed in claim 1, wherein at least one part of the plurality of diagnostic radiation sources shares the diagnostic radiation detector.

10. A radiation therapy device comprising:
a housing; and
a therapeutic radiation source that is arranged in the housing and rotated in a plane,
wherein a diagnostic radiation source and a diagnostic radiation detector are arranged such that diagnostic X-ray radiation, which is directed by the diagnostic radiation source onto the diagnostic radiation detector, travels at an angle through the plan; and
wherein the diagnostic radiation source is located on one side of the plane, and a center of the diagnostic radiation detector is located on another side of the plane.

11. The radiation therapy device as claimed in claim 10, wherein the diagnostic radiation source is arranged locationally fixed with respect to the radiation therapy device.

12. The radiation therapy device as claimed in claim 10, wherein the diagnostic radiation source is an X-ray source, which is based on carbon nanotubes.

13. The radiation therapy device as claimed in claim 10, wherein a plurality of diagnostic radiation sources are arranged locationally fixed in the radiation therapy device, such that diagnostic X-ray radiation, which emanates from the plurality of diagnostic radiation sources passes through an object to be examined from different directions.

14. The radiation therapy device as claimed in claim 11, wherein the diagnostic radiation source is an X-ray source, which is based on carbon nanotubes.

15. The radiation therapy device as claimed in claim 11, wherein a plurality of diagnostic radiation sources are arranged locationally fixed with respect to the radiation therapy device, such that diagnostic X-ray radiation, which emanates from the plurality of diagnostic radiation sources, passes through an object to be examined from different directions.

16. The radiation therapy device as claimed in claim 2, further comprising a control unit configured to control the plurality of diagnostic radiation sources and to read out the diagnostic radiation detector in coordination with the control of the plurality of diagnostic radiation sources, such that a plurality of projection image data for the object are generated from different directions.

17. The radiation therapy device as claimed in claim 3, further comprising a circular gantry having a central opening, in which the object to be examined is arranged,
wherein the therapeutic radiation source, the plurality of diagnostic radiation sources and the diagnostic radiation detector are arranged inside a housing of the circular gantry.

18. The radiation therapy device as claimed in claim 7, wherein the plurality of diagnostic radiation sources are arranged in circular fashion in the radiation therapy device, and wherein the object to be examined is positioned inside the circular arrangement of the plurality of diagnostic radiation sources.

19. The radiation therapy device as claimed in claim 10, wherein the diagnostic radiation source is arranged in the same housing as the therapeutic radiation source.

20. The radiation therapy device as claimed in claim 11, wherein the diagnostic radiation source is arranged locationally fixed with respect to the radiation therapy device such that the diagnostic radiation source does not rotate when the therapeutic radiation source rotates.

21. The radiation therapy device as claimed in claim 10, further comprising:
a plurality of diagnostic radiation sources, the plurality of diagnostic radiation sources comprising the diagnostic radiation source; and
additional diagnostic radiation detectors,
wherein at least one part of the plurality of diagnostic radiation sources shares the diagnostic radiation detector,
wherein the diagnostic radiation detector and the additional diagnostic radiation detectors are arranged in circular fashion around an object to be examined, and
wherein another part of the plurality of diagnostic radiation sources is associated with each of the diagnosis radiation detector and the additional diagnostic radiation detectors.

22. A radiation therapy device comprising:
a therapeutic radiation source;
an imaging unit, the imaging unit comprising:
a plurality of diagnostic radiation sources, from which diagnostic X-ray radiation is directed onto an object to be examined, wherein the plurality of diagnostic radiation sources are X-ray sources, which are based on carbon nanotubes; and
a diagnostic radiation detector, with which the diagnostic X-ray radiation is detected after passing through the object to be examined; and
additional diagnostic radiation detectors,
wherein at least one part of the plurality of diagnostic radiation sources shares the diagnostic radiation detector,
wherein the diagnostic radiation detector and the additional diagnostic radiation detectors are arranged in circular fashion around the object to be examined, and
wherein another part of the plurality of diagnostic radiation sources is associated with each of the diagnostic radiation detector and the additional diagnostic radiation detectors.

* * * * *